US00PP28085P2

(12) United States Plant Patent
Eveleens

(10) Patent No.: US PP28,085 P2
(45) Date of Patent: Jun. 6, 2017

(54) ***HYDRANGEA* PLANT NAMED 'HORTMANI'**

(50) Latin Name: *Hydrangea macrophylla*
Varietal Denomination: HORTMANI

(71) Applicants: Horteve Breeding BV, Aalsmeer (NL); Kolster Holding BV, Boskoop (NL)

(72) Inventor: Cornelis Pieter Eveleens, Aalsmeer (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 50 days.

(21) Appl. No.: 14/757,043

(22) Filed: Nov. 12, 2015

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea macrophylla* named 'HORTMANI' that is characterized by its globular shaped inflorescences, its smaller sized inflorescences, its sterile flowers with sepals that are very dark pink in color, and its floriferous habit.

2 Drawing Sheets

Botanical classification: *Hydrangea macrophylla.*
Varietal denomination: 'HORTMANI'.

CROSS REFERENCE TO RELATED APPLICATIONS

This application is co-pending with U.S. Plant Patent Applications filed for plants derived from the same breeding program that are entitled *Hydrangea* Plant Named 'HORTMADACE' (U.S. Plant patent application Ser. No. 14/757,047).

BACKGROUND OF THE INVENTION

The present invention relates to a new and distinct cultivar of *Hydrangea macrophylla* and will be referred to hereafter by its cultivar name, 'HORTMANI'. 'HORTMANI' represents a new mophead type *Hydrangea*, a deciduous shrub grown for use as a landscape plant, potted plant and as a cut flower.

The new cultivar was derived from a controlled breeding program conducted by the Inventor in Boskoop, The Netherlands. The objective of the breeding program is to develop new cultivars of *Hydrangea* with good cut flower qualities with unique flower colors. The objective with this new cultivar was to obtain a plant with sturdy red flowers with good color retention as they mature.

The Inventor made a cross in April 2006 between unnamed and unpatented plants in the Inventor's breeding program; reference no. 03-027-03 as the female parent and reference no. 03-066-05 as the male parent. The Inventor selected 'HORTMANI', in June 2013 as a single unique plant amongst the seedlings that resulted from the above cross.

Asexual propagation of the new cultivar was first accomplished by the Inventor by softwood stem cuttings in Boskoop, The Netherlands in August 2009. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMANI' as a unique cultivar of *Hydrangea*.

1. 'HORTMANI' exhibits globular shaped inflorescences.
2. 'HORTMANI' exhibits smaller sized inflorescences.
3. 'HORTMANI' exhibits sterile flowers with sepals that are very dark pink in color.
4. 'HORTMANI' exhibits a floriferous habit.

The female parent of 'HORTMANI', reference no. 03-027-03, differs from 'HORTMANI' in having sepals with a sturdier substance that are darker in color, in having fewer inflorescences, and in having a taller plant height. The male parent of 'HORTMANI', reference no. 03-066-05, differs from 'HORTMANI' in having sterile flower sepals that are weaker in substance and in having a taller plant height. 'HORTMANI' can be most closely compared to the cultivars 'HORTMADACE' and 'Horo' (not patented). 'HORTMADACE' is similar to 'HORTMANI' in being a good container plant and in being floriferous. 'HORTMADACE' differs from 'HORTMANI' in having sepals that are redder in color, in having less inflorescences and in having larger inflorescences. 'Horo' is similar to 'HORTMANI' in having sepals that are similar in color. 'Horo' differs from 'HORTMANI' in having longer stem internodes lengths, in having larger and fewer inflorescences, and in having sterile sepals with a sturdier substance.

BRIEF DESCRIPTION OF THE DRAWINGS

The accompanying colored photographs illustrate the overall appearance and distinct characteristics of the new *Hydrangea*, 'HORTMANI'. The photographs were taken of a two year-old plant as grown in a greenhouse in a 15-liter container in Boskoop, The Netherlands.

The photograph in FIG. 1 provides a side view of a plant of 'HORTMANI'.

Figure 1:
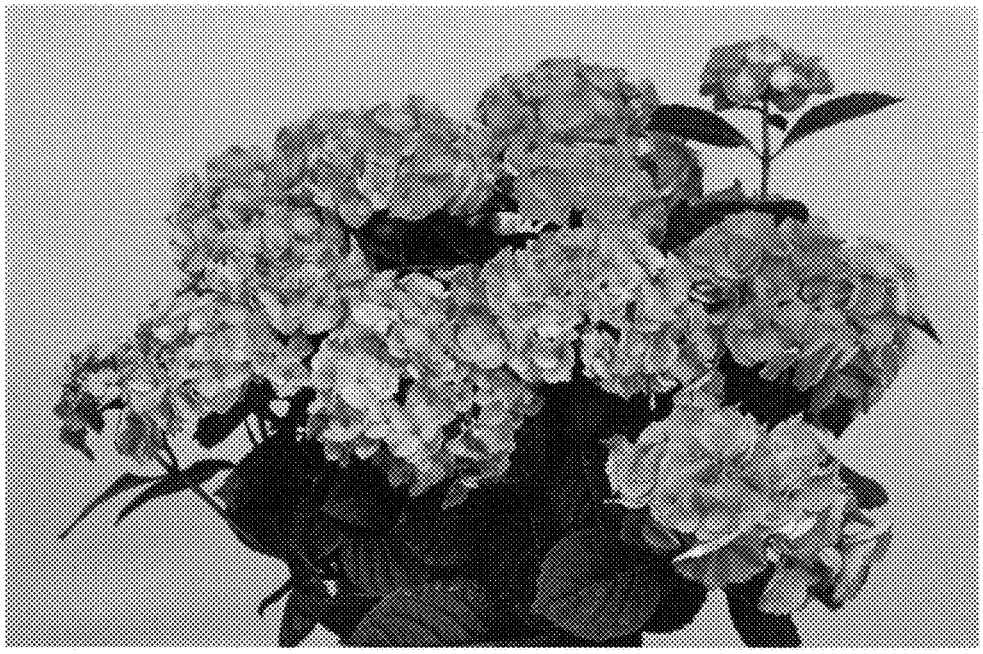
Figure 2:
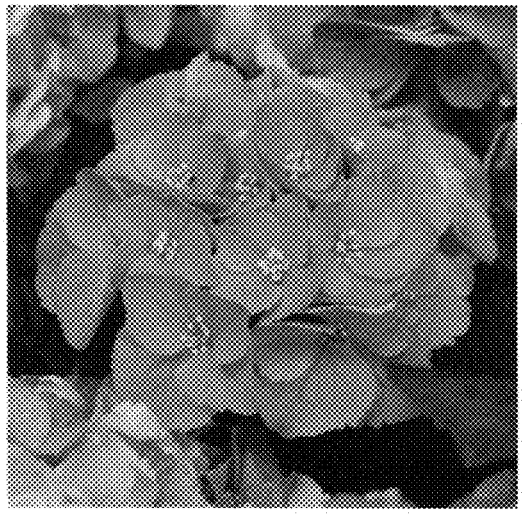

The photograph in FIG. 2 provides a close-up view of an inflorescence of 'HORTMANI'.

Figure 3:
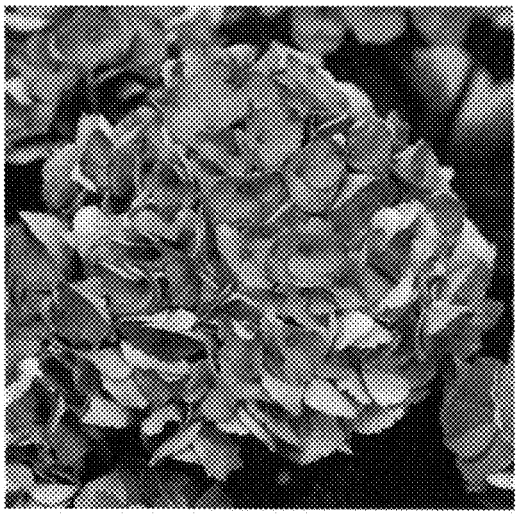

The photograph in FIG. 3 provides a close-up view of a faded inflorescence of 'HORTMANI'.

Figure 4:
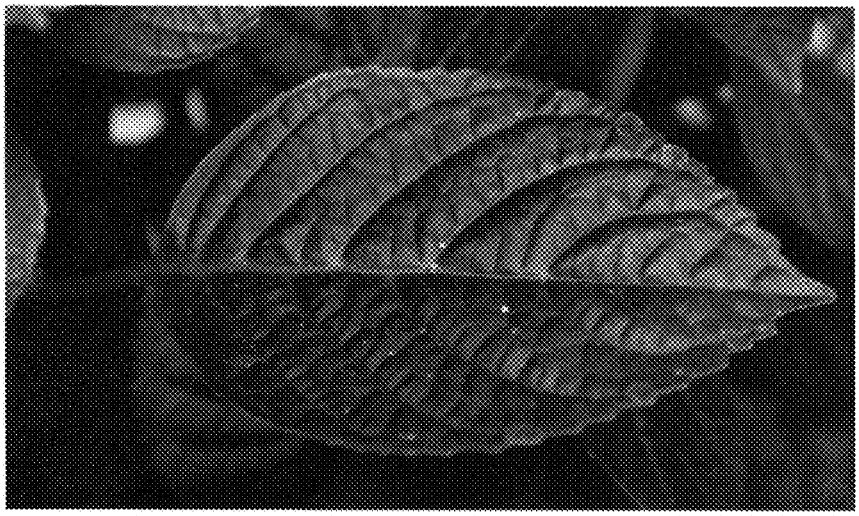

The photograph in FIG. 4 provides a close-up view of the foliage of 'HORTMANI'.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of 'HORTMANI' as grown in a greenhouse in 1.5-liter containers in June in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Blooms from May to August as greenhouse grown plants in Boskoop, the Netherlands.

*Plant type.*—Deciduous shrub, mophead type *Hydrangea.*

*Plant habit.*—Broad spreading upright.

*Height and spread.*—Reaches about 43.6 cm in height and 54.6 cm in spread and 1 m in height and 1 m in spread as grown in the landscape.

*Hardiness.*—At least in U.S.D.A. Zones 5 to 9.

*Diseases resistance.*—No particular susceptibility or resistance to diseases or pests has been observed.

*Root description.*—Fine and fibrous.

*Propagation.*—Softwood stem cuttings.

*Root development.*—An average of 6 months at average air temperatures of 15° to 25° C. to finish a young plant.

*Growth rate and vigor.*—Moderate.

Stem description:

*Stem shape.*—Rounded.

*Stem strength.*—Strong.

*Stem color.*—New growth; 144A, mature growth; color between N186A and 203A.

*Stem size.*—Average of 19.2 cm (excluding inflorescence) in length and 4 mm in diameter.

*Stem surface.*—Glabrous, moderately glossy, sparsely to moderately lenticellate, lenticles; 5 per $cm^2$, an average of 1.5 mm in length and 1 mm in width, 187A in color.

*Internode length.*—Average of 3.7 cm.

*Branching.*—Average of 18 lateral branches without pinching, freely branching.

Foliage description:

*Leaf shape.*—Broad ovate to broadly elliptic.

*Leaf arrangement.*—Opposite.

*Leaf division.*—Simple.

*Leaf base.*—Short attenuate.

*Leaf apex.*—Apiculate.

*Leaf margins.*—Serrate.

*Leaf venation.*—Pinnate, upper surface color; 144A, lower surface color; 144A to 144B.

*Leaf size.*—Matures to an average of 8.4 cm in length and 6.3 cm in width.

*Leaf attachment.*—Petiolate.

*Leaf surface.*—Upper surface; glabrous, rugose and slightly glossy, lower surface; glabrous, rugose and matte.

*Leaf color.*—Young foliage upper surface; between 141A and 143A, young foliage lower surface; 143A, mature upper surface; between 139A and 147A, mature lower surface; 137B.

*Petioles.*—An average of 2.1 cm in length and 3 mm in diameter, color; upper surface and lower surface 144A, surface moderately glossy.

Inflorescence description:

*Inflorescence type.*—Terminal panicle, mophead in form comprised of a center region of fertile flowers surrounded by single sterile flowers.

*Lastingness of inflorescence.*—Persistent, pink coloration retained for about 6 weeks (depending on growing conditions).

*Lastingness as a cut flower.*—Pink coloration color is retained for 2 weeks as a fresh cut and for several months as an aged dried flower.

*Inflorescence substance.*—Moderately sturdy sterile flowers.

*Inflorescence number.*—One per lateral or sublateral stem if pinched.

*Inflorescence size.*—Average of 8.6 cm in height and 12.7 cm in diameter.

*Flower number.*—Average of 125 sterile flowers and 15 fertile flowers per panicle.

*Flower fragrance.*—None.

*Flower aspect.*—Upright to outward.

*Flower size.*—Sterile flowers; an average of 3.3 cm in diameter and 1.4 cm in depth, fertile flowers; an average of 1 cm in diameter and 6 mm in depth.

*Flower type.*—Rotate.

*Flower buds.*—Sterile flowers; average of 8 mm in length and 7 mm in diameter prior to opening, obovate in shape, 144C to 145A in color, fertile flowers; average of 5 mm in length and 4 mm in diameter, broad obovate in shape, color; 62A, base is 144C, tinged 63B.

*Peduncles.*—Moderately strong, average of 4 cm in length and 2 mm in width, blend of 144A and N186D in color, surface is dull and glabrous.

*Pedicels.*—Sterile flowers; held at an average angle of 50° to main peduncle, an average of 2.2 cm in length and 1.5 mm in diameter, strong strength, 64B in color, surface matte, and moderately covered with short soft hairs an average of 0.1 mm in length and width and too small to measure color, fertile flowers; held at an average angle of 10° from vertical, an average of 3 mm in length and 1 mm in diameter, N186D in color, moderate strength, and moderately covered with short soft hairs an average of 0.1 mm in length and width, too small to measure color.

*Petals.*—Sterile flowers; average of 4, rotate in arrangement, ovate and concave in shape, entire margin, acute apex, cuneate base, average of 2.5 mm in length and 1.5 mm in width, upper surface glabrous and matte, lower surface glabrous and slightly glossy, color of upper surface when opening and when fully opened; N74C and N74D, not fading, dropped shortly after maturity, color of lower surface when opening and when fully opened; 75C, base N74C and N74D, not fading, dropped shortly after maturity, fertile flowers; an average of 4, rotate arrangement, acute apex, cuneate base, entire margins, ovate and slightly concave in shape, an average of 2.5 mm in length and 1.5 mm in width, upper surface; glabrous and matte, lower surface; glabrous and slightly glossy, color; upper surface when opening N74C to N74D, lower surface when opening 75C, base N74C to N74D, upper and lower surface when fully opened; petals of fertile flowers are dropped when maturing.

*Sepals*.—Sterile flowers; average of 4-5, rotate arrangement, reniform to broad deltoid in shape, an average of 1.8 cm in length and 2.3 cm in width, broad bluntly acute apex, obtuse to very short broad attenuate base, upper surface very slightly rugose, glabrous and matte, lower surface glabrous and matte, serrate margins, color when opening; upper surface N57A, 58B and 145C, lower surface 63B, color when fully opened; upper surface 58B with apex 63B, lower surface 63C, color when fading; upper surface 182B and tinged with 146C, lower surface 195B and tinged with 182B, fertile flowers; 5, rotate in arrangement, ovate in shape, entire margin, acute apex, broad cuneate base, average of 1 mm in length and 0.8 mm in width, both surfaces are glabrous and matte, color of upper and lower surface when opening 144C, color of upper surface when fully open 144C and tinged with 63B, color of lower surface when fully open 145C and tinged with 63C.

Reproductive organs: (Present on fertile flowers and sterile flowers).

*Stamens*.—Sterile flowers; average of 8, anther is broad kidney-shaped, an average of 0.75 mm in length and 197C in color, filament is 4 mm in length and 76B in color, pollen is moderate in quantity and 155A in color, fertile flowers; average of 8, anther is broad kidney-shaped, 0.75 mm in length and 197C in color, filament is 4 mm in length and 70B in color, pollen is moderate in quantity and 155A in color.

*Pistils*.—Sterile flowers; average of 3, an average of 0.5 mm in length, stigma is club-shaped and 76A in color, style is an average of 0.5 mm in length and 75B in color, ovary is 64C in color, fertile flowers; average of 3, an average of 0.5 mm in length, stigma is club-shaped and 76A in color, style is an average of 0.5 mm in length and 75B in color, ovary is 64C in color.

*Fruit and seed*.—Has not been observed to date.

It is claimed:

1. A new and distinct cultivar of *Hydrangea* plant named 'HORTMANI' substantially as herein illustrated and described.

* * * * *